United States Patent
Morales Correa

(10) Patent No.: US 11,595,589 B2
(45) Date of Patent: Feb. 28, 2023

(54) SURGICAL CAMERA SYSTEM WITH HIGH DYNAMIC RANGE

(71) Applicant: Arthrex, Inc., Naples, FL (US)

(72) Inventor: Efrain O. Morales Correa, Santa Ynez, CA (US)

(73) Assignee: ARTHREX, INC., Naples, FL (US)

(*) Notice: Subject to any disclaimer, the term of this patent is extended or adjusted under 35 U.S.C. 154(b) by 0 days.

(21) Appl. No.: 17/383,250

(22) Filed: Jul. 22, 2021

(65) Prior Publication Data
US 2023/0021812 A1  Jan. 26, 2023

(51) Int. Cl.
*H04N 5/235* (2006.01)
*A61B 1/00* (2006.01)
*H04N 5/225* (2006.01)

(52) U.S. Cl.
CPC ....... *H04N 5/2355* (2013.01); *A61B 1/00013* (2013.01); *A61B 1/000095* (2022.02); *H04N 5/2353* (2013.01); *H04N 2005/2255* (2013.01)

(58) Field of Classification Search
CPC ............... H04N 5/2355; H04N 5/2353; H04N 2005/2255; A61B 1/00009; A61B 1/00013
See application file for complete search history.

(56) References Cited

U.S. PATENT DOCUMENTS

| | | |
|---|---|---|
| 8,606,009 B2 | 12/2013 | Sun |
| 8,723,978 B2 | 5/2014 | Kwon et al. |
| 8,947,555 B2 | 2/2015 | Velarde |
| 8,977,073 B2 | 3/2015 | Kwon et al. |
| 9,020,257 B2 | 4/2015 | El-Mahdy et al. |
| 9,055,231 B2 | 6/2015 | Garten |
| 9,160,936 B1* | 10/2015 | Rivard ................. H04N 5/2355 |
| 9,432,589 B2 | 8/2016 | Kuang et al. |
| 9,489,706 B2 | 11/2016 | Levy et al. |

(Continued)

FOREIGN PATENT DOCUMENTS

WO   2021/010174   1/2021

OTHER PUBLICATIONS

"Bayer patterned high dynamic range image reconstruction using adaptive weighting function" by Hee Kang, et al., EURASIP Journal on Advances in Signal Processing 2014:76, pp. 1-18.

(Continued)

*Primary Examiner* — Ahmed A Berhan
(74) *Attorney, Agent, or Firm* — Karish & Bjorgum, PC

(57) ABSTRACT

An endoscopic camera device having an optical assembly; a first image sensor in optical communication with the optical assembly, the first image sensor receiving a first exposure and transmitting a first low dynamic range image; a second image sensor in optical communication with the optical assembly, the second image sensor receiving a second exposure and transmitting a second low dynamic range image, the second exposure being higher than the first exposure; and a processor for receiving the first low dynamic range image and the second low dynamic range image; wherein the processor is configured to combine the first low dynamic range image and the second dynamic range image into a high dynamic range image using a luminosity value derived as a preselected percentage of a cumulative luminosity distribution of at least one of the first low dynamic range image and the second low dynamic range image.

17 Claims, 5 Drawing Sheets

(56) References Cited

U.S. PATENT DOCUMENTS

| | | |
|---|---|---|
| 9,509,918 B2 | 11/2016 | Liu et al. |
| 9,584,732 B2 | 2/2017 | Romaneko |
| 9,811,890 B2 | 11/2017 | Blonde et al. |
| 9,852,499 B2 | 12/2017 | Ming et al. |
| 10,366,478 B2 | 7/2019 | Hu et al. |
| 10,924,689 B1 * | 2/2021 | Duckett, III ........... H04N 5/238 |
| 2004/0004666 A1 | 1/2004 | Sano |
| 2008/0284872 A1 | 11/2008 | Asoma |
| 2018/0336669 A1 | 11/2018 | Mertens |
| 2020/0081235 A1 | 3/2020 | Takahashi |
| 2020/0134787 A1 | 4/2020 | Bouzaraa et al. |
| 2020/0400498 A1 | 12/2020 | Talbert et al. |
| 2022/0268942 A1 | 8/2022 | Kaizu et al. |

OTHER PUBLICATIONS

"Detail-Enhanced Multi-Scale Exposure Fusion" by Zhengguo Li, et al., IEEE Transactions on Image Processing vol. 26, Issue: 3, Published Jan. 16, 2017, pp. 1243-1252.

"Multi-exposure image fusion based on wavelet transform", by Wenlong Zhang, et al., International Journal of Advanced Robotic Systems, Mar.-Apr. 2018, pp. 1-19.

"High Dynamic Range Image Generation Based on Convolutional Weight Optimization Robust to Mixed Noise Removal", by Ryo Matsuoka, et al., APSIPA Annual Summit and Conference 2018, 978-988-14768-5-2, Nov. 12-15, 2018, Hawaii, pp. 1066-1070.

"A Precise Multi-Exposure Image Fusion Method Based on Low-level Features", by Guanqiu Qi, Sensors 2020, 20, 1597, pp. 1-18.

International Search Report and Written Opinion, dated Nov. 14, 2022, pp. 1-21.

* cited by examiner

SURGICAL CAMERA SYSTEM WITH HIGH DYNAMIC RANGE

BACKGROUND

The present disclosure relates to devices used in endoscopic surgery and, more particularly, to an endoscopic camera system with high dynamic range.

The dynamic range of a scene may be defined as a ratio of the radiances of the brightest part of the scene and the darkest part of the scene. These radiances are detected by an imaging sensor, which has an intrinsic dynamic range. The intrinsic dynamic range can be defined as the ratio of the maximum detected scene radiance to the minimum detected scene radiance. The maximum is strongly dependent on pixel well depth and the minimum is strongly dependent on dark current noise and read noise.

Intrinsic dynamic range may be increased by lowering dark current noise and read noise, but there are limits to how much further lowering of dark current noise and read noise is possible. Intrinsic dynamic range may also be increased by raising the pixel well depth. One way to raise pixel well depth is to use large pixels, but that is not possible for applications that require small form factors and high resolution. It is desirable to have images with greater dynamic range than the intrinsic dynamic range of most existing image sensors.

Therefore, there exists a need for a system and method of providing high dynamic range images that remedies the shortcomings of the prior art.

SUMMARY

This disclosure is directed to systems and methods for combining two low dynamic range images into a single high dynamic range image using a blending parameter calculated based on a predetermined percentage of luminosity values in at least one of the low dynamic range images.

In an embodiment, an endoscopic camera device has: an optical assembly; a first image sensor in optical communication with the optical assembly, the first image sensor receiving a first exposure and transmitting a first low dynamic range image; a second image sensor in optical communication with the optical assembly, the second image sensor receiving a second exposure and transmitting a second low dynamic range image, the second exposure being higher than the first exposure; and a processor coupled to the first image sensor and the second image sensor for receiving the first low dynamic range image and the second low dynamic range image. The processor is configured to combine the first low dynamic range image and the second dynamic range image into a high dynamic range image using a luminosity value derived as a preselected percentage of a cumulative luminosity distribution of at least one of the first low dynamic range image and the second low dynamic range image.

In an implementation, the processor is further configured to generate a luminosity histogram and to analyze the luminosity histogram to determine a cumulative distribution of pixel values. The processor may be further configured to generate the histogram from a largest luminosity value of each pixel of the first low dynamic range image. The processor may be further configured to generate the histogram from the green value of each pixel of the first low dynamic range image.

In an implementation, the processor selects a luminosity value representing a preselected percentage of the cumulative luminosity distribution of between about 50 percent and about 90 percent. The processor may select a luminosity value representing a preselected percentage of the cumulative luminosity distribution of between about 60 percent and about 80 percent. The processor may select a luminosity value representing a preselected percentage of the cumulative luminosity distribution of about 70 percent.

In an implementation, the first image sensor receives about from about 10 percent to about 20 percent of the visible light and the second image sensor receives from about 80 percent to about 90 percent of the visible light. In an implementation, the processor selects a luminosity value from the second low dynamic range image.

The present disclosure is also directed to a method of generating high dynamic range image. In an implementation, a method of generating a high dynamic range image has the steps of: receiving a first low dynamic range image having a first exposure; receiving a second low dynamic range image having a second exposure, the second exposure being higher than the first exposure; generating a luminosity histogram from at least one of the first dynamic range image and the second low dynamic range image; analyzing the luminosity histogram to determine a cumulative distribution of pixel values; determining a pixel value corresponding to a predetermined percentage of the cumulative distribution of pixel values; using the determined pixel value to calculate a blending parameter; and blending the first low dynamic range image and second low dynamic range image into a high dynamic range image using the blending parameter.

In an implementation, the predetermined percentage of the cumulative distribution of pixel values is between about 50 percent and about 90 percent. The predetermined percentage of the cumulative distribution of pixel values may be between about 60 percent and about 80 percent. The predetermined percentage of the cumulative distribution of pixel values may be about 70 percent.

In an implementation, the first low dynamic range image is used to generate the luminosity histogram. In an implementation, the second low dynamic range image is used to generate the luminosity histogram. The luminosity histogram may be generated from a largest luminosity value of each pixel. The luminosity histogram may also be generated from the green value of each pixel.

In an implementation, an endoscopic camera device has: an optical assembly; a first image sensor in optical communication with the optical assembly, the first image sensor receiving a first exposure and transmitting a first low dynamic range image; a second image sensor in optical communication with the optical assembly, the second image sensor receiving a second exposure and transmitting a second low dynamic range image, the second exposure being higher than the first exposure; and a processor coupled to the first image sensor and the second image sensor for receiving the first low dynamic range image and the second low dynamic range image. The processor is configured to: generate a luminosity histogram from a highest luminosity value of each pixel of the first low dynamic range image; analyze the luminosity histogram to determine a cumulative luminosity distribution of pixel values; determine a luminosity value corresponding to a predetermined percentage of the cumulative luminosity distribution of pixel values; and combine the first low dynamic range image and the second dynamic range image into a high dynamic range image using the determined luminosity value.

These and other features are described below.

BRIEF DESCRIPTION OF THE DRAWINGS

The features, aspects and advantages of the present invention will become better understood with regard to the following description, appended claims and accompanying figures wherein:

DETAILED DESCRIPTION

In the following description of the preferred implementations, reference is made to the accompanying drawings which show by way of illustration specific implementations in which the invention may be practiced. Wherever possible, the same reference numbers will be used throughout the drawings to refer to the same or like parts. It is to be understood that other implementations may be utilized and structural and functional changes may be made without departing from the scope of this disclosure.

The present disclosure is directed to a system and method for producing a high dynamic range image using a weighted sum of two low dynamic range images. The first low dynamic range image has a lower exposure than the second low dynamic range image. The summing weights are monotonic functions of one of the low dynamic range images, and the monotonic functions are characterized by a single parameter. The single parameter is chosen automatically by pre-selecting a fixed percentage of the cumulative sum distribution of one of the low dynamic range images.

Figure 1:
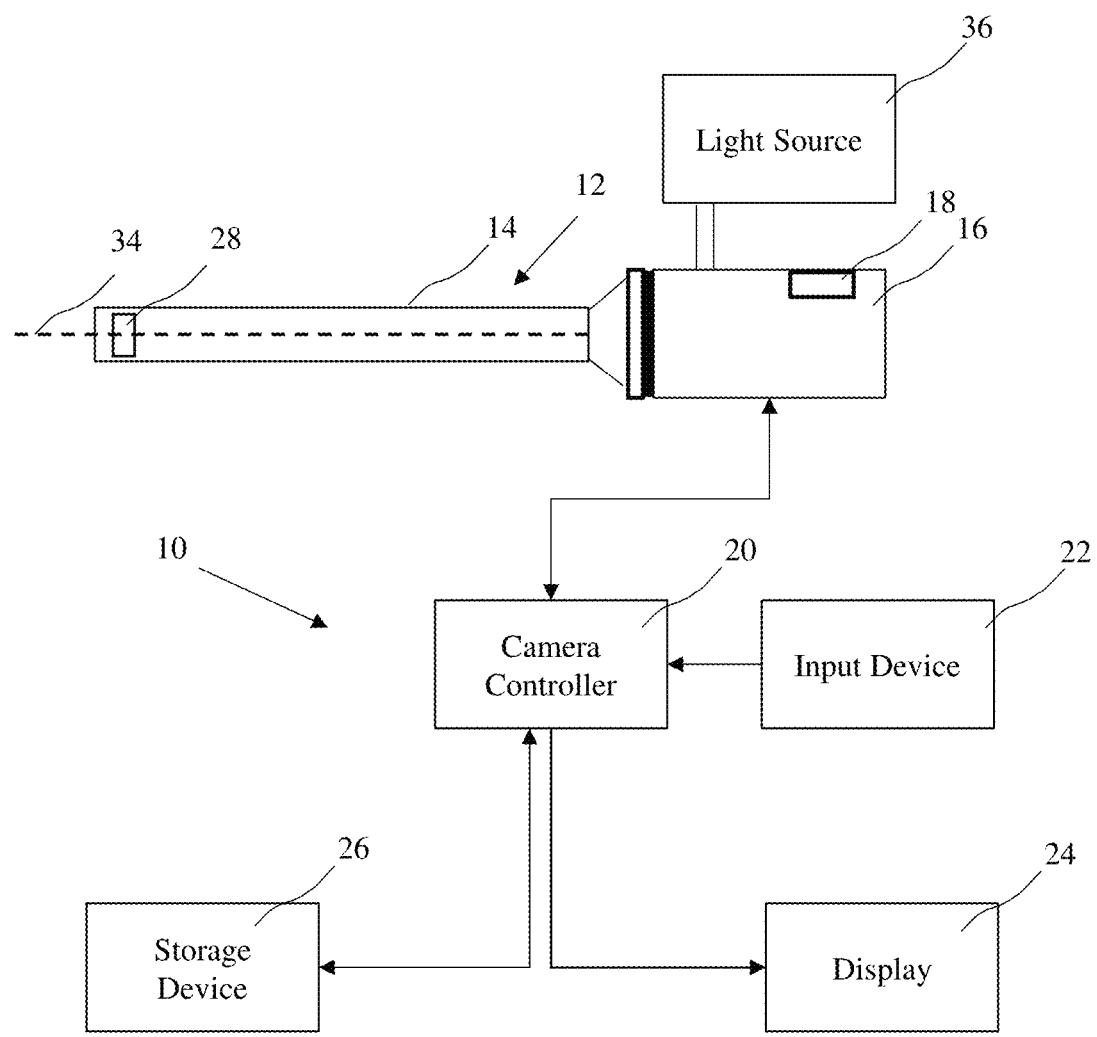
FIG. 1 is a schematic diagram of an endoscopic camera system according to an implementation.
Figure 2:
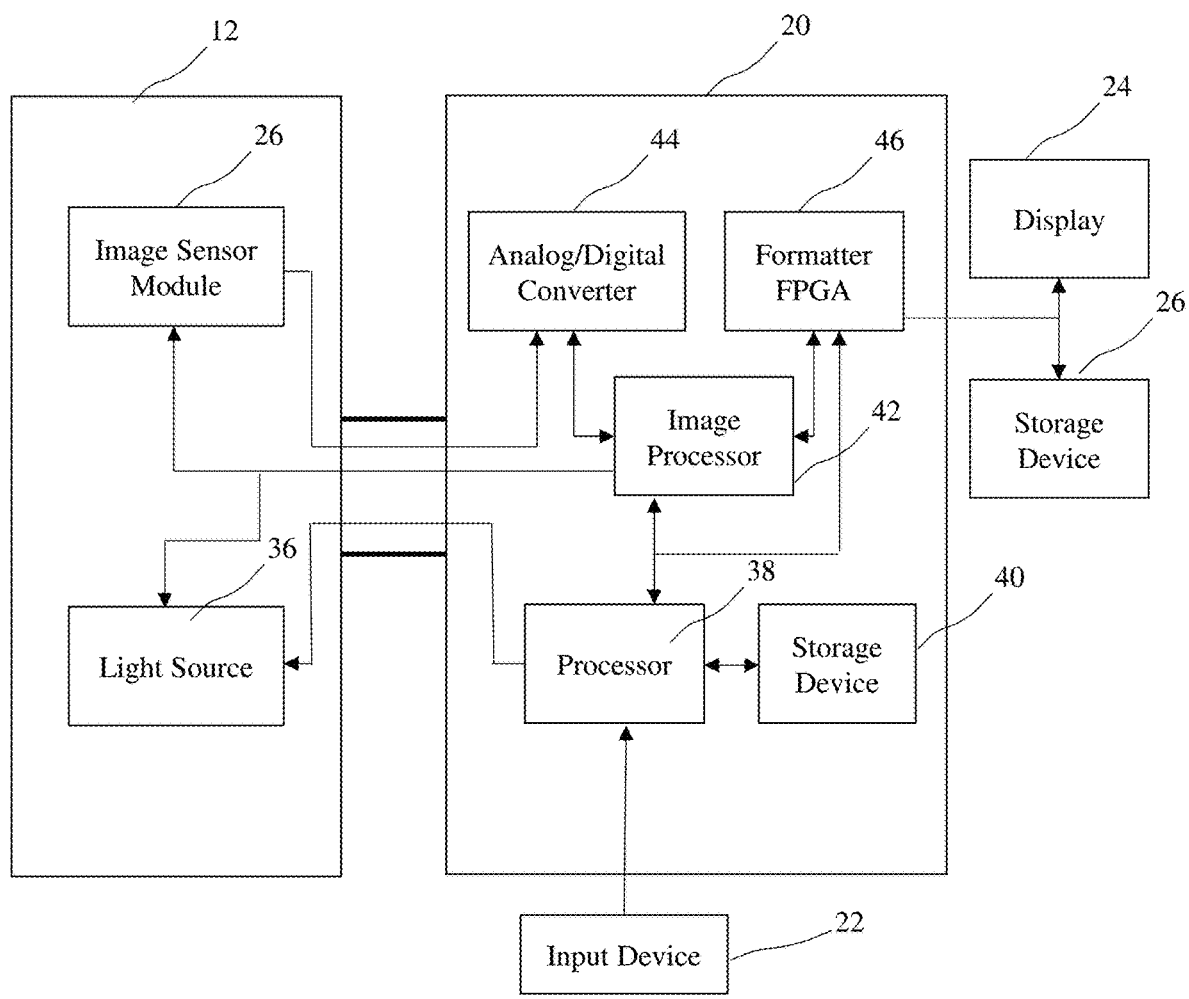
FIG. 2 is a further schematic diagram of an endoscopic camera system according to an embodiment.
Figure 3:
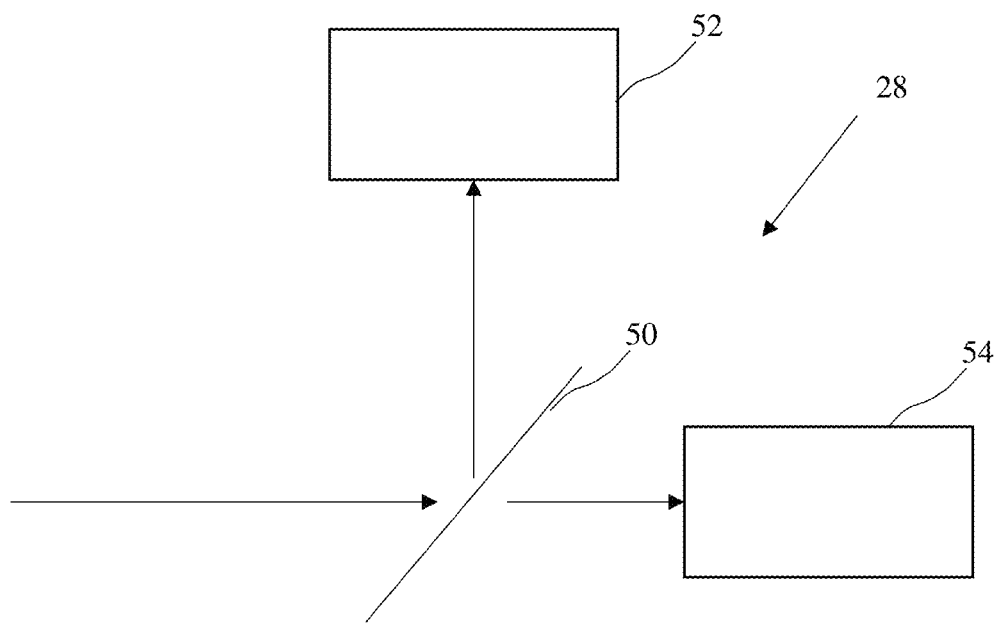
FIG. 3 is schematic diagram of an image sensor module usable in the endoscopic camera systems of FIGS. 1 and 2.

With reference to FIGS. 1 to 3, an endoscopic camera system 10 according to an implementation has a camera 12. The camera 12 has a shaft 14 couplable to a handpiece 16. The handpiece 16 may have an input device 18, such as buttons, switches or dials. The handpiece 16 is connectable to a camera controller 20 ("CCU" or "camera controller"). The handpiece 16 and the camera controller 20 may be connected via wire to facilitate data transfer between the camera and the camera controller. The camera 12 and the camera controller 20 may also be wirelessly connected to facilitate data transfer, such as via IEEE 802.11b or IEEE 802.11n or ultra-wide band (UWB). The camera controller 20 may be connectable to at least one input device 22 such as a mouse, keyboard, touchpad, or touchscreen monitor. Additionally, the camera controller 20 may be connectable to a display 24 and a storage device 26, such as for storing images.

An image sensor module 28 may be positioned inside the shaft 14 and proximal to a distal tip 30 of the shaft 12. Additionally, the camera 12 may be coupled to a light source 36. The light source 36 may be inside of the camera 12.

The light source 36 includes a lamp. The lamp may be, for example, a semiconductor light source such as laser or LED to illuminate the field of view. The light source 36 is configured to appropriately illuminate the field of view of the video camera. Further, the light generated as well as camera sensitivity may extend beyond the visible spectrum. The illumination may be intended to excite fluorescence directly in a target, or in a fluorescent substance such as indocyanine green, that is then sensed by the camera. For example, the light source 36 might produce illumination in the near infrared (NIR) range and the camera sense the fluorescence at a longer IR wavelength. The illumination and camera sensitivity could extend from UV to NIR continuously or be composed of separate narrow bands.

Referring to FIG. 2, the camera controller 20 is preferably a programmable unit containing sufficient processing capacity to accommodate a wide range of control, user interface and image acquisition/processing functions. The camera controller 20 has a processor 38 that runs program applications providing for a variety of capabilities. For instance, an image capture and display capability allows for both display of a live feed of an image through the display 24 coupled to the camera controller 20, as well as image capture. Captured images may be stored, such as in an internal storage device 40 or external storage device 26, or transmitted to other devices.

An image processor 42 controls and processes the output from the image sensing module 28. Although other controllers and processors may be used to control and process the output from the image sensing module 28, use of one or more FPGAs for processing video images allows the system to achieve precise timing to generate a standard video output signal. User interface logic and possible external network connectivity may be performed by software running on the processor 38.

In an implementation, analog RGB data is transmitted from the image sensor module 28 to the camera controller 20. The Analog RGB data passes through an Analog/Digital converter 44 to the image processor 42 where the video is processed. The processed video is then passed to a video output that may include a formatter FPGA 46 where the video is formatted into various display formats. The formatter FPGA 46 may also overlay information, such as patient and/or doctor information, onto the video. The formatted video may be converted to an analog signal for display. The formatted video is sent to the display 24 and/or the storage device 26. Alternatively, an Analog/Digital converter may be located in the camera head and digital RGB data transmitted from the camera head 12 to the camera controller 20. Additionally, the image sensors may include Analog/Digital converters.

The camera controller 20 issues commands to the camera 12 to adjust its operating characteristics, and the camera 12 may send confirmation to the camera controller 20 that the camera received the commands. The image processor 42 and/or the processor 38 may communicate with a shutter driver either in the camera controller 20 or the camera 12 to control an exposure period of the image sensing module 28. Additionally, the image processor 42 and/or the processor 38 communicates with the light source 32 to control the drive current to the lamp of the light source 32.

A schematic diagram of the image sensor module 28 according to an implementation is shown in FIG. 3. The image sensor module 28 has an optical element 50, such as a prism or a mirror, that directs light onto a first image sensor 52 and a second image sensor 54. Each of the first image sensor 52 and the second image sensor 54 may be, for example, a charge couple device (CCD) sensor or complementary metal oxide semiconductor (CMOS) sensor. The image sensor module 28 may also contain additional optical elements and image sensors such as for sensing of near infrared light. The first and second image sensors need not be identical and may have different characteristics.

In an implementation, the image sensors receive differential amounts of light. The optical element 50 may direct light so that the first image sensor 52 receives a lower exposure, and is therefore a low exposure sensor that generates a low exposure image, and the second image sensor 54 receives a higher exposure, and is therefore a high exposure sensor that generates a high exposure image. In an implementation, the optical element directs between about 10% and about 40% of light to the first image sensor 52 and between about 60% to about 90% of light to the second image sensor 54. In an implementation, the optical element directs between about 10% and about 20% of light to the first image sensor 52 and between about 80% to about 90% of light to the second image sensor 54. In an implementation, the optical element directs about 10% of light to the first image sensor 52 and about 90% of light to the second image sensor 54.

Alternatively, the first image sensor 52 may receive a higher exposure and the second image sensor 54 may receive a lower exposure. Each of the first image sensor 52 and the second image sensor 54 generate relatively low dynamic range images. The images from both sensors are combined and to create a single image with a high dynamic range.

Key issues are how to select which pixels of each low dynamic range image are used to create a combined high dynamic range image and how those pixels are blended together. Rather than manually selecting blending parameters or automatically blending the images based on an arbitrary blending parameter, blending parameters are chosen based on scene content by pre-selecting a fixed percentage of the cumulative luminosity distribution of at least one of the low dynamic range images.

Figure 4:
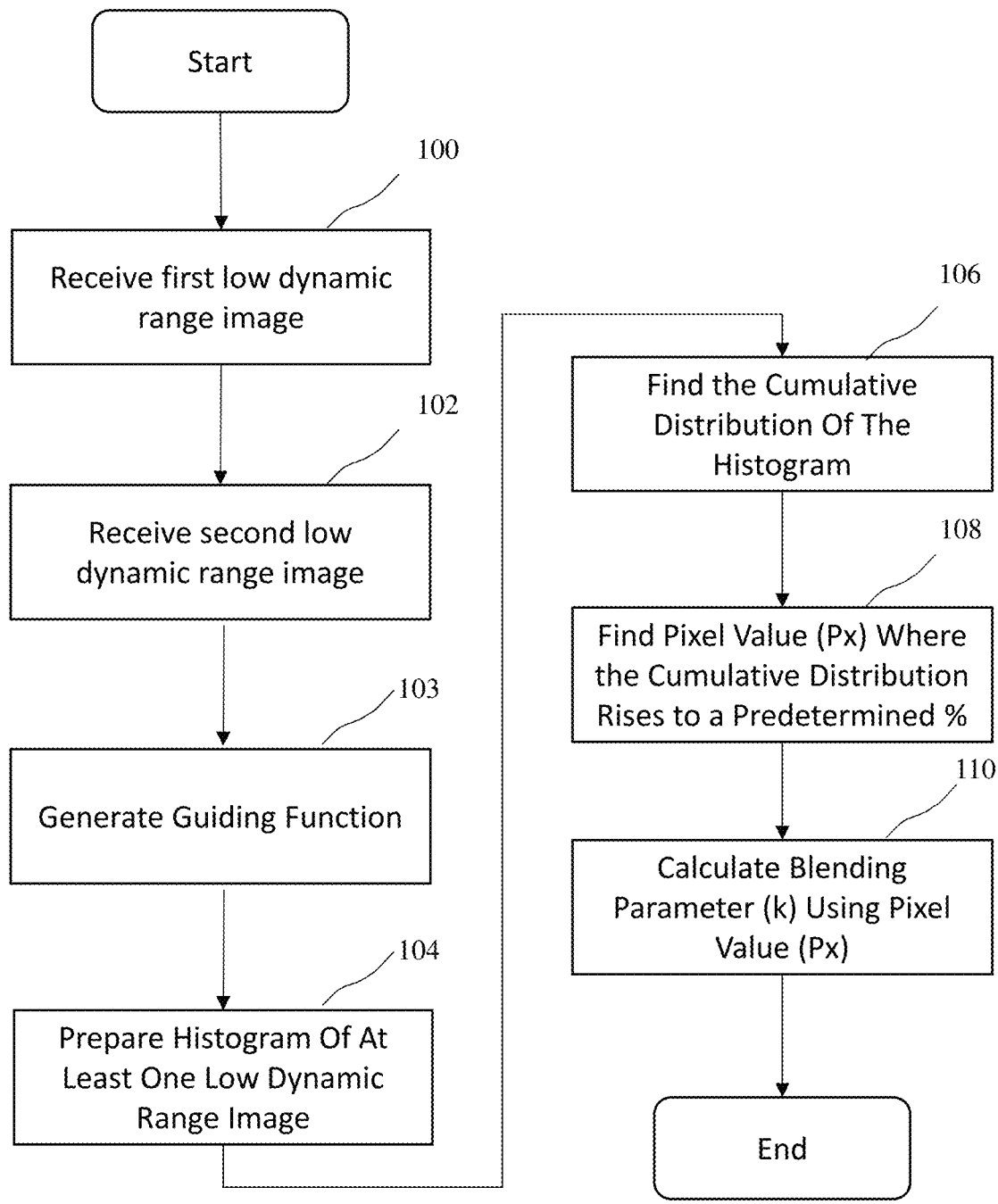
FIG. 4 is a flowchart showing a method for calculating a blending parameter for combining two low dynamic range images into a high dynamic range image according to an implementation.
Figure 5:
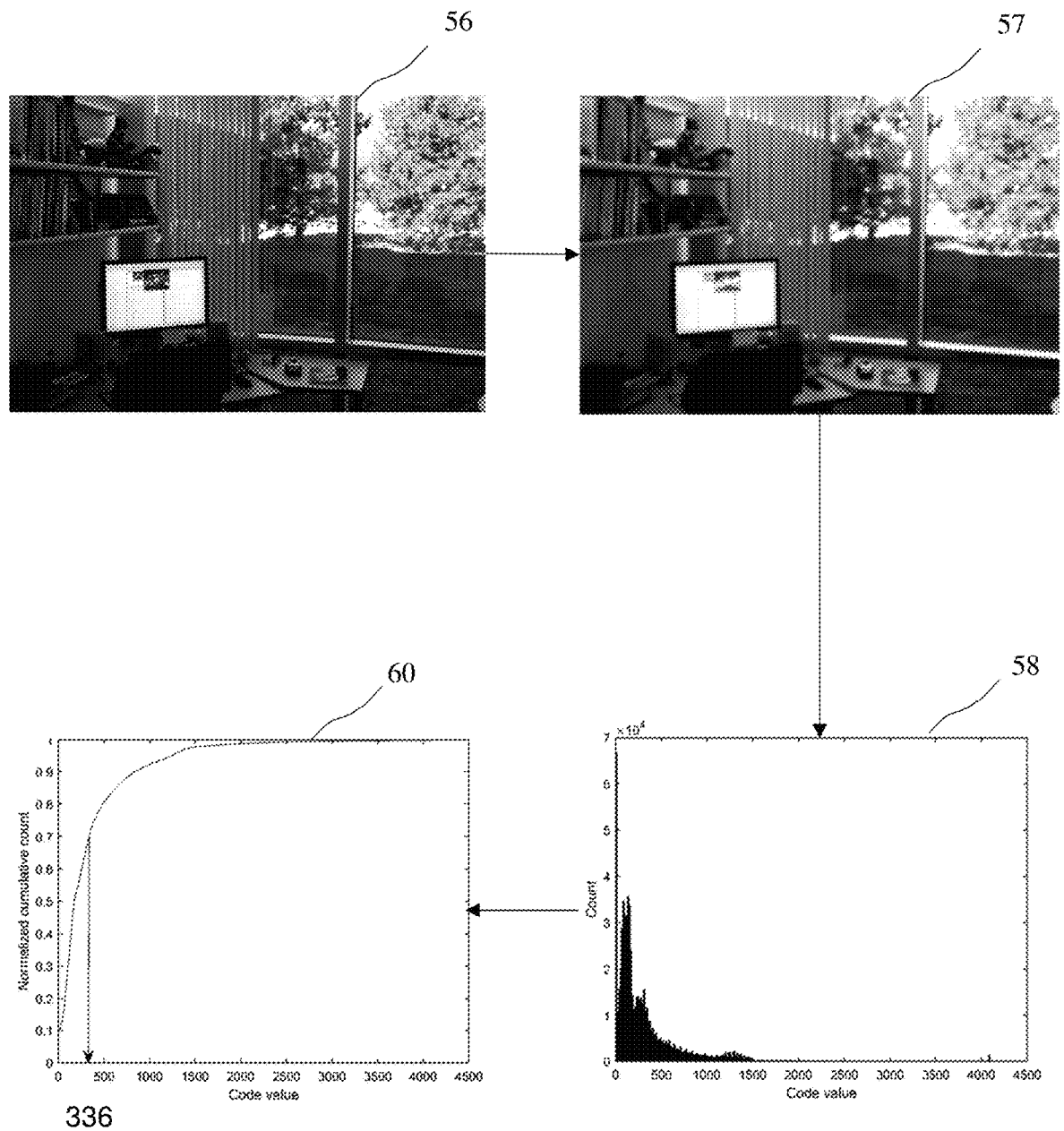
FIG. 5 shows a graphical implementation of a portion of the method of FIG. 4.

FIG. 4 is a flowchart illustrating a method for determining blending parameters according to an implementation. FIG. 5 is a graphical representation of at least a portion of the steps of FIG. 4. A first low dynamic range image is received by the image processor 42 from the first image sensor 52 in step 100. A second low dynamic range image is received by the image processor 42 from the second image sensor 54 in step 102. The image processor 42 generates from at least one of the first low dynamic range image or the second low dynamic range image a luminosity image called a guiding function 57 in step 103. In step 104, the image processor 42 generates a luminosity histogram 58 from the guiding function 57, which depicts the distribution of captured luminosity. For purposes of illustrating an implementation, the histogram 58 is generated from the low exposure image.

Each pixel of a color image may comprise three values. In an implementation, the three values represent red, green, and blue. In an implementation, the guiding function is generated by finding the largest of the three values of each pixel regardless of whether the largest value is red, green or blue. The luminosity histogram is then generated from the guiding function. The possible luminosity values are grouped into bins. In an implementation, the luminosity values are grouped into 256 different bins. The horizontal axis of the histogram 58 represents bins of different luminosity values and the vertical axis represents the total number of pixels within each particular luminosity value bin.

Alternatively, the histogram 58 may be generated by considering only the green pixel values of the image. Alternatively, the histogram 58 may be generated using a weighted average of red, green, and blue colors at each pixel. In an implementation, the luminosity value for each pixel is calculated using the formula 0.3 (Red)+0.59 (Green)+0.11 (Blue).

In a distribution analysis step 106, the histogram is analyzed to determine a cumulative distribution of pixel luminosity values, as shown in graph 60. In an analysis step 108, the cumulative distribution of pixel luminosity values is analyzed to determine a corresponding pixel value (Px) at a preselected percentage of luminosity values. The luminosity value percentage is preselected so that a corresponding pixel value may be found automatically. However, the corresponding pixel value will change depending on the overall scene luminosity distribution and this allows the system and method to automatically adapt to different scenes.

The percentage is preselected to prevent dynamic range gaps between the different images to be combined, and also so that most useful pixels that should have an influence on the final high dynamic range image are not marginalized. In an implementation, the pre-determined percentage of pixels used from a low exposure image is between about 50 and about 90 percent, and more preferably between about 60 and about 80 percent, and more preferably about 70 percent.

As seen in FIG. 5, for the example image analyzed, the luminosity value below which about 70 percent of the pixels were measured was 336 and 336 is the corresponding pixel value (Px). As discussed below, the pixel value is then used to generate a blending parameter so that the pixels having that luminosity or more from the low exposure image are weighted more heavily in the combined HDR image and the remaining pixels from the high exposure image are weighted more heavily. The luminosity value below which a percentage of the pixels fall varies depending on the overall luminosity of the images.

The two low dynamic range images are combined using the formula:

$$I_{HDR}(x,y;c) = W_{hi}(x,y;c)I_{hi}(x,y;c) + W_{lo}(x,y;c)I_{lo}(x,y;c)$$
$$= e^{kf_{lo}(x,y;c)}I_{hi}(x,y;c) + (1-e^{kf_{lo}(x,y;c)})I_{lo}(x,y;c).$$

$I_{HDR}$ is the high dynamic range image;
$W_{hi}$ is the weighting function for the high exposure image;
$I_{hi}$ is the value of a given pixel in the high exposure image;
$W_{lo}$ is the weighting function for the low exposure image;
$I_{lo}$ is the value of a given pixel in the low exposure image;
x and y are the pixel coordinates
$c \in \{R,G,B\}$
The negative blending parameter k controls the position of the transition point between the two regions where each image dominates.

$f_{lo}$ is a guiding function that depends on $I_{lo}$.

Blending is done pixel by pixel for each color separately to generate a single blended image with a high dynamic range. Other implementations may use color spaces other than RGB in which to perform the blending, for example, YCbCr.

In an additional implementation the high exposure image may be used to calculate the blending parameter using the following equations:

$$I_{HDR}(x,y;c) = W_{hi}(x,y;c)I_{hi}(x,y;c) + W_{lo}(x,y;c)I_{lo}(x,y;c)$$
$$= e^{kf_{hi}(x,y;c)}I_{hi}(x,y;c) + (1-e^{kf_{hi}(x,y;c)})I_{lo}(x,y;c).$$

The variables are the same, but the guiding function $f_{hi}$ depends on $I_{hi}$ instead of $I_{lo}$.

In a calculation step 110, the corresponding pixel value (Px) is used to calculate the blending parameter (k). In an implementation the blending parameter (k) is calculated using the formula k=ln(0.50)/Px.

In a preferred implementation, the weighting function for the high exposure image, $W_{hi}$, is $e^{kf_{lo}}$, although other monotonically decreasing functions could be selected. So, in the example shown in FIG. 5, the cumulative histogram has a value of 70% at a luminosity of 336. Using the expression $W_{hi}=e^{kf_{lo}}$ then $0.50=e^{k*336}$ and k=ln(0.50)/336=−0.002. This value of k defines the luminosity of 336 as the point of equal weights, that is, the luminosity where $W_{hi}=W_{lo}=0.5$.

In an implementation a low-pass filter is applied to the guiding function before using it in order to avoid the guiding function reacting to small details. The low pass filter can be expressed as $f'_{hi}(x,y;c)$=gaussian $(f_{hi}(x,y;c))$, although other low-pass operations may be used. In an implementation the guiding function incorporates an edge function to use blurred and unblurred guiding functions to attenuate the effect over hard edges. The edge function can be expressed as: $W_{lo}(x,y;c)=(e^{kf'_{hi}}(x,y;c)+e^{kf_{hi}}(x,y;c))/2$, although other approaches like multi-level pyramid or wavelet decompositions may be used.

The system and method disclosed herein is advantageous because it is computationally simple compared to other methods and therefore may be carried out faster and with less processing power. Additionally, in systems where a blending parameter is pre-selected and fixed (without an automatic method to select the single parameter such as disclosed herein), then depending on the scene content and the exposure differences between the two low dynamic range images, the produced high dynamic range mage may not be a visually-pleasing image.

There is disclosed in the above description and the drawings, a system and method for making high dynamic range images that fully and effectively overcomes the disadvantages associated with the prior art. However, it will be apparent that variations and modifications of the disclosed implementations may be made without departing from the principles of the invention. The presentation of the implementations herein is offered by way of example only and not limitation, with a true scope and spirit of the invention being indicated by the following claims.

Any element in a claim that does not explicitly state "means" for performing a specified function or "step" for performing a specified function, should not be interpreted as a "means" or "step" clause as specified in 35 U.S.C. § 112.

What is claimed is:

1. An endoscopic camera device comprising:
   an optical assembly;
   a first image sensor in optical communication with the optical assembly, the first image sensor receiving a first exposure and transmitting a first low dynamic range image;
   a second image sensor in optical communication with the optical assembly, the second image sensor receiving a second exposure and transmitting a second low dynamic range image, the second exposure being higher than the first exposure; and
   a processor coupled to the first image sensor and the second image sensor for receiving the first low dynamic range image and the second low dynamic range image;
   wherein the processor is configured to combine the first low dynamic range image and the second dynamic range image into a high dynamic range image using a luminosity value derived as a preselected percentage of a cumulative luminosity distribution of at least one of the first low dynamic range image and the second low dynamic range image; and
   wherein the processor is further configured to generate a luminosity histogram and to analyze the luminosity histogram to determine a cumulative distribution of pixel values.

2. The endoscopic camera device of claim 1 wherein the processor is further configured to generate the histogram from a highest luminosity value of each pixel of the first low dynamic range image.

3. The endoscopic camera device of claim 1 wherein the processor is further configured to generate the histogram from the green value of each pixel of the first low dynamic range image.

4. The endoscopic camera device of claim 1 wherein the processor selects a luminosity value representing a preselected percentage of the cumulative luminosity distribution of between about 50 percent and about 90 percent.

5. The endoscopic camera device of claim 1 wherein the processor selects a luminosity value representing a preselected percentage of the cumulative luminosity distribution of between about 60 percent and about 80 percent.

6. The endoscopic camera device of claim 1 wherein the processor selects a luminosity value representing a preselected percentage of the cumulative luminosity distribution of about 70 percent.

7. The endoscopic camera device of claim 1 wherein the first image sensor receives from about 10 percent to about 20 percent of the visible light and the second image sensor receives from about 80 percent to about 90 percent of the visible light.

8. The endoscopic camera device of claim 1 wherein the processor selects a luminosity value from the second low dynamic range image.

9. A method of generating a high dynamic range image comprising the steps of:
   receiving a first low dynamic range image having a first exposure;
   receiving a second low dynamic range image having a second exposure, the second exposure being higher than the first exposure;
   generating a luminosity histogram from at least one of the first dynamic range image and the second low dynamic range image;
   analyzing the luminosity histogram to determine a cumulative distribution of pixel values;
   determining a pixel value corresponding to a predetermined percentage of the cumulative distribution of pixel values;
   using the determined pixel value to calculate a blending parameter; and
   blending the first low dynamic range image and second low dynamic range image into a high dynamic range image using the blending parameter.

10. The method of claim 9 wherein the predetermined percentage of the cumulative distribution of pixel values is between about 50 percent and about 90 percent.

11. The method of claim 9 wherein the predetermined percentage of the cumulative distribution of pixel values is between about 60 percent and about 80 percent.

12. The method of claim 9 wherein the predetermined percentage of the cumulative distribution of pixel values is about 70 percent.

13. The method of claim 9 wherein the first low dynamic range image is used to generate the luminosity histogram.

14. The method of claim 9 wherein the second low dynamic range image is used to generate the luminosity histogram.

15. The method of claim 9 wherein the luminosity histogram is generated from a highest luminosity value of each pixel.

16. The method of claim 9 wherein the luminosity histogram is generated from the green value of each pixel.

17. An endoscopic camera device comprising:
- an optical assembly;
- a first image sensor in optical communication with the optical assembly, the first image sensor receiving a first exposure and transmitting a first low dynamic range image;
- a second image sensor in optical communication with the optical assembly, the second image sensor receiving a second exposure and transmitting a second low dynamic range image, the second exposure being higher than the first exposure; and
- a processor coupled to the first image sensor and the second image sensor for receiving the first low dynamic range image and the second low dynamic range image;
- wherein the processor is configured to:
  - generate a luminosity histogram from a highest luminosity value of each pixel of the first low dynamic range image;
  - analyze the luminosity histogram to determine a cumulative luminosity distribution of pixel values;
  - determine a luminosity value corresponding to a predetermined percentage of the cumulative luminosity distribution of pixel values; and
  - combine the first low dynamic range image and the second dynamic range image into a high dynamic range image using the determined luminosity value.

* * * * *